United States Patent
Goedecke

(10) Patent No.: US 8,866,073 B2
(45) Date of Patent: Oct. 21, 2014

(54) ION TRAP MOBILITY SPECTROMETER AND METHOD OF USING THE SAME

(71) Applicant: Morpho Detection, LLC, Newark, CA (US)

(72) Inventor: Lyndon Karl Goedecke, Everett, MA (US)

(73) Assignee: Morpho Detection, LLC, Newark, CA (US)

( * ) Notice: Subject to any disclaimer, the term of this patent is extended or adjusted under 35 U.S.C. 154(b) by 0 days.

(21) Appl. No.: 14/194,279

(22) Filed: Feb. 28, 2014

(65) Prior Publication Data

US 2014/0264002 A1 Sep. 18, 2014

Related U.S. Application Data

(60) Provisional application No. 61/800,044, filed on Mar. 15, 2013.

(51) Int. Cl.
*H01J 49/00* (2006.01)

(52) U.S. Cl.
USPC ............ 250/282; 250/281; 250/283; 250/288

(58) Field of Classification Search
USPC .................................. 250/281, 282, 283, 288
See application file for complete search history.

(56) References Cited

U.S. PATENT DOCUMENTS

| | | | |
|---|---|---|---|
| 5,200,614 A | 4/1993 | Jenkins | |
| 5,491,337 A | 2/1996 | Jenkins et al. | |
| 6,690,005 B2 | 2/2004 | Jenkins et al. | |
| 6,765,198 B2 | 7/2004 | Jenkins et al. | |
| 6,831,272 B2 | 12/2004 | Mack et al. | |
| 2002/0005479 A1* | 1/2002 | Yoshinari et al. | 250/288 |
| 2005/0205775 A1 | 9/2005 | Bromberg et al. | |
| 2006/0163472 A1* | 7/2006 | Marquette | 250/290 |
| 2007/0158548 A1 | 7/2007 | Haigh | |
| 2008/0087818 A1 | 4/2008 | Li | |
| 2008/0179515 A1 | 7/2008 | Sperline | |

FOREIGN PATENT DOCUMENTS

| | | |
|---|---|---|
| EP | 1178307 A1 | 2/2002 |
| EP | 1271610 A2 | 1/2003 |

OTHER PUBLICATIONS

GE Security, Ion Trap Mobility Spectrometry: The Science Behind the Technology, 2008, 6 pages, GE Homeland Protection, Inc.
An extended European Search Report, dated Jun. 27, 2014, for co-pending EP patent application No. EP 14000925.9 (6 pgs.).

* cited by examiner

*Primary Examiner* — Nicole Ippolito
(74) *Attorney, Agent, or Firm* — Armstrong Teasdale LLP

(57) ABSTRACT

An apparatus for detecting constituents in a sample includes a casing and an ionization chamber defined by the casing. The apparatus also includes an ion collector positioned downstream of the ionization chamber. The apparatus further includes a spectral analysis device coupled to the ion collector. The spectral analysis device is configured to generate a detection spectrum representative of ions collected at the ion collector. The detection spectrum includes an analyte peak portion and a peak tailing portion. The apparatus also includes a control system that is configured to generate a first pulse having a first polarity to initiate a discharge of stored ions from the ionization chamber. The control system is also configured to generate a second pulse substantially immediately after the first pulse. The second pulse has a second polarity opposite the first polarity and is configured to reduce the peak tailing portion.

20 Claims, 11 Drawing Sheets

ION TRAP MOBILITY SPECTROMETER AND METHOD OF USING THE SAME

CROSS REFERENCE TO RELATED APPLICATIONS

This application claims the priority of Provisional Patent Application Ser. No. 61/800,044, entitled "ION TRAP MOBILITY SPECTROMETER AND METHOD OF USING THE SAME", which was filed on Mar. 15, 2013, and is hereby incorporated by reference in its entirety.

BACKGROUND OF THE INVENTION

The embodiments described herein relate generally to an ion trap mobility spectrometer (ITMS) and, more particularly, to an ITMS for enhancing detection of materials of interest through enhanced resolution of high-mobility ions and low-mobility ions.

At least some known spectroscopic detection devices include ion trap mobility spectrometer (ITMS) detection systems. Such ITMS detection systems are used to detect trace portions of materials of interest, e.g., residues. At least some known ITMS detection systems include an ionization chamber that produces positive ions, negative ions, and free electrons. As the ions are being generated in the ionization chamber to increase the ion population therein, a retaining grid is maintained at a slightly greater potential than the electric field in the ionization chamber to induce a retention field and reduce the potential for ion leakage from the chamber. An electric field is then induced across the ionization chamber and, depending on the polarity of the induced electric field, the positive ions or the negative ions are pulsed from the ionization chamber, through a high-voltage "kickout pulse", into a drift region through the retaining grid. The ions are transported through the drift region to a collector electrode. Signals representative of the ion population at the collector electrode are generated and transmitted to an analysis instrument and/or system to determine the constituents in the collected gas samples.

The population of ions generated in the ionization chamber include low-mobility analytes and high-mobility analytes. The low-mobility analytes traverse the drift region with a lower velocity than the high-mobility analytes due to their relatively lower mass than the lighter high-mobility analytes. The low-mobility and high-mobility analytes pulsed into the drift region from the ionization chamber typically form an ion disk with a predetermined axial width value and possibly a trailing ion tail. Such trailing ion tail defines an asymmetric peak trace on spectral analysis equipment that negatively impacts the subsequent analysis of the peak trace. The ideal peak trace for spectral analysis is perfectly symmetrical.

Further, in many known ITMS detection systems, as the disk of ions traverses the drift region, the separation of the high-mobility analytes from the low-mobility analytes induces expansion and distortion of the ion disk. The high-mobility analytes form a disk that transits faster than a disk formed of low-mobility analytes and the disks may overlap as they are received at the collector electrode. The peaks on the trace thus generated on the spectral analysis equipment is distorted with poor resolution and are difficult to analyze. Moreover, in many of the known ITMS detection systems, there is no precise control over the width of the ion disk injected into the drift region. Fundamentally, this is due to inconsistent, and sometimes, incomplete clearing out of the ionization chamber due to nonhomogeneity of the electric field induced in the ionization chamber, e.g., low field regions at the back of the ionization chamber.

Increasing the strength of the electric field to empty the ionization chamber more rapidly and to decrease the transit time through the drift region increases the potential for ion leakage from the ionization chamber through the retainer grid after the kickout pulse. Such ion loss decreases the resolution of the spectral peaks to be analyzed. Increasing the width of the kickout pulse to eject a greater number of slow ions of interest without losing a significant portion to the retention grid may increase the width of the detected peaks of the reactant ions and analyte peaks of interest. Such an increase in peak width decreases the resolution of the analyses in the region typically associated with HME substances.

Further, increasing the field strength for a kickout pulse of reduced width to eject both high-mobility ions and low-mobility ions may result in the ions just inside the chamber proximate the retention grid to induce an electric field of their own that opposes the retention field generated by the retention grid. Moreover, if the kickout pulse is reduced in width, a significant ion tail develops on the ion disk. The peak trace also develops an asymmetric peak trace on the spectral analysis equipment due to the detection peaks associated with ions continuing to leak through the retention grid following cessation of the pulse as the ions just inside the grid create a field of their own in opposition to the retention voltage field. As such, the resolution of the instrument/system is reduced.

BRIEF DESCRIPTION OF THE INVENTION

In one aspect, an apparatus for detecting constituents in a sample is provided. The apparatus includes a casing and an ionization chamber at least partially defined by the casing. The ionization chamber is configured to generate and store ions. The apparatus also includes an ion collector positioned downstream from the ionization chamber. The apparatus further includes a spectral analysis device coupled to the ion collector. The spectral analysis device is configured to generate a detection spectrum representative of ions collected at the ion collector. The detection spectrum includes an analyte peak portion and a peak tailing portion. The apparatus also includes a control system coupled to the ionization chamber. The control system is configured to generate a first pulse within the ionization chamber having a first polarity to initiate a discharge of at least a portion of the stored ions from the ionization chamber. The control system is also configured to generate a second pulse within the ionization chamber having a second polarity opposite the first polarity of the first pulse generated substantially immediately after the first pulse. The second pulse is configured to reduce the peak tailing portion.

In another aspect, a method of detecting constituents in a sample is provided. The method includes channeling a sample gas stream to be tested for constituents into an ionization chamber and generating a plurality of ions in the ionization chamber. The method also includes storing the plurality of ions in the ionization chamber. The method further includes inducing a first electric field across the ionization chamber for a first temporal period. The first electric field has a first polarity and at least a portion of the ions are ejected from the ionization chamber. The method also includes inducing a second electric field across the ionization chamber substantially immediately following the first temporal period. The second electric field has a second polarity opposite the first polarity. The ejection of the at least a portion of the ions from the ionization chamber is substantially decreased.

BRIEF DESCRIPTION OF THE DRAWINGS

FIG. 1 is a schematic view of an exemplary ion trap mobility spectrometer (ITMS) detection system;

FIG. 2 is a schematic view of a portion of an exemplary control system that may be used with the ITMS detection system shown in FIG. 1;

FIG. 3 is a schematic view of another portion of the control system that may be used with the ITMS detection system shown in FIG. 1;

FIG. 4 is a graphical view of a positive mode control voltage waveform that may be used with the control system shown in FIGS. 2 and 3;

FIG. 5 is a graphical view of a negative mode control voltage waveform that may be used with the control system shown in FIGS. 2 and 3;

FIG. 6 is a graphical view of positive mode control voltage waveforms for fast ions and slow ions that may be used with the control system shown in FIGS. 2 and 3;

FIG. 7 is a graphical view of a primary reactant peak trace generated by the ITMS detection system shown in FIG. 1 without a reverse pulse;

FIG. 8 is a graphical view of the primary reactant peak trace without a reverse pulse shown in FIG. 7 with a primary reactant peak resulting from adding the reverse pulse superimposed thereon;

FIG. 9 is a magnified graphical view of a portion of the primary reactant peak trace resulting from adding the reverse pulse shown in FIG. 8;

FIG. 10 is a magnified graphical view of a portion of the primary reactant peak trace shown in FIG. 9 with a magnified view of a portion of the primary reactant peak without a reverse pulse shown in FIG. 7 superimposed thereon; and FIG. 11 is a graphical view of positive mode control voltage waveforms for fast ions and slow ions that may be used with the control system shown in FIGS. 2 and 3 and resultant spectra optimized for high-mobility and low-mobility ions.

DETAILED DESCRIPTION OF THE INVENTION

The embodiments described herein provide a cost-effective system and method for improving detection of materials of interest from an object or person. The systems and methods described herein induce a first electric field across an ionization chamber for a first temporal period, i.e., a first pulse. The first pulse has a first polarity, thereby ejecting at least a portion of the ions from the ionization chamber. Also, the systems and methods described herein induce a second electric field across the ionization chamber substantially immediately following the first temporal period. The second electric field has a second polarity opposite the first polarity, i.e., a second pulse, thereby substantially decreasing the ejection of the at least a portion of the ions from the ionization chamber. Further, the systems and methods described herein reduce a tailing portion of a spectral peak associated with the ions ejected from the ionization chamber as a result of the second field pulse. Moreover, the first and second pulses are regulated such that more precise ion injection is achieved and increased resolution of high-mobility analytes is facilitated.

Figure 1:
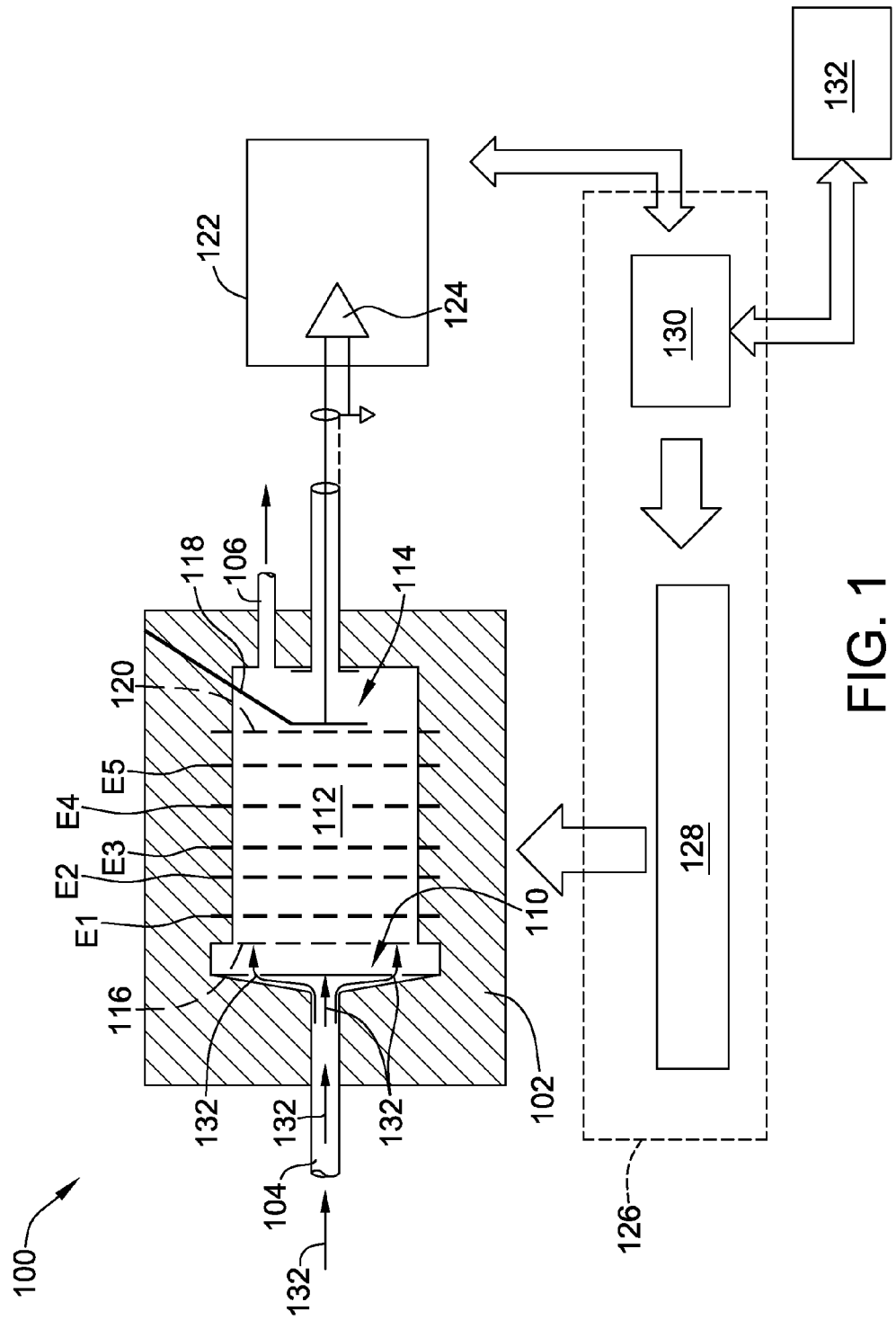
FIGS. 1-11 show exemplary embodiments of the systems and methods described herein.

FIG. 1 is a schematic view of an exemplary ion trap mobility spectrometer (ITMS) detection system 100. ITMS detection system 100 includes a casing 102. ITMS detection system 100 also includes a gas inlet tube 104 and a gas outlet tube 106 coupled to casing 102. Casing 102 defines a diffuser region 108 coupled in flow communication with gas inlet tube 104. Casing 102 also defines an ion trap reactor, i.e., an ionization chamber 110 coupled in flow communication with diffuser region 108. Ionization chamber 110 includes an ionizing source material (not shown), e.g., and without exception, nickel-63 ($^{63}$Ni) that emits low-energy beta-($\beta$-) particles. Alternatively, any ionizing source material that enables operation of ITMS detection system 100 as described herein is used. Casing 102 further defines a drift field region 112 coupled in flow communication with ionization chamber 110. Casing 102 also defines a collector region 114 coupled in flow communication with drift field region 112 and gas outlet tube 106. ITMS detection system 100 further includes a first retaining grid 116 extending over an outlet end of ionization chamber 110.

ITMS detection system 100 further includes a series of sequential annular electrodes E1, E2, E3, E4, and E5 extending about drift region 112. ITMS detection system 100 also includes an ion collector, i.e., a collector electrode 118 and a second grid, i.e., a collector shield grid 120 positioned just upstream of collector electrode 118. Collector electrode 118 is coupled to a spectral analysis device 122 that includes at least one current-to-voltage amplifier 124. ITMS detection system 100 also includes an ITMS control system 126 that includes a control circuit 128 and a processing device 130. Control circuit 128 is coupled to ionization chamber 110, retaining grid 116, sequential annular electrodes E1, E2, E3, E4, and E5, and collector shield grid 120. Processing device 130 is operatively coupled to spectral analysis device 122 and control circuit 128.

As used herein, the terms "processor" and "processing device" are not limited to just those integrated circuits referred to in the art as a computer, but broadly refers to a microcontroller, a microcomputer, a programmable logic controller (PLC), an application specific integrated circuit, and other programmable circuits, and these terms are used interchangeably herein. In the embodiments described herein, memory may include, but is not limited to, a computer-readable medium, such as a random access memory (RAM), and a computer-readable non-volatile medium, such as flash memory. Alternatively, a floppy disk, a compact disc-read only memory (CD-ROM), a magneto-optical disk (MOD), and/or a digital versatile disc (DVD) may also be used. Also, in the embodiments described herein, additional input channels may be, but are not limited to, computer peripherals associated with an operator interface such as a mouse and a keyboard. Alternatively, other computer peripherals may also be used that may include, for example, but not be limited to, a scanner. Furthermore, in the exemplary embodiment, additional output channels may include, but not be limited to, an operator interface monitor.

Processing device 130 and other processors (not shown) as described herein process information transmitted from a plurality of electrical and electronic devices that include, without limitation, spectral analysis device 122 and control circuit 128. Memory devices (not shown) and storage devices (not shown) store and transfer information and instructions to be executed by processing device 130. Such memory devices and storage devices can also be used to store and provide temporary variables, static (i.e., non-volatile and non-changing) information and instructions, or other intermediate information to processing device 130 during execution of instructions by processing device 130. Instructions that are executed include, but are not limited to, analysis of signals transmitted from spectral analysis device 122. The execution of sequences of instructions is not limited to any specific combination of hardware circuitry and software instructions. ITMS detection system 100 also includes a data storage device 132 coupled to processing device 130. Data storage device 132 stores the data generated by processing device 130, such data also retrievable through processing device 130.

In operation, a collection device (not shown) is coupled to gas inlet tube 104 and collects gaseous samples 132 from an object of interest (not shown). In some embodiments, rather than gaseous samples, inlet tube 104 channels particulate samples that are then vaporized to generate gaseous samples 132. Gaseous samples 132 are channeled to diffuser region 108 for expanding gaseous samples 132 prior to entry into ionization chamber 110. $^{63}$Ni emits low-energy β-particles into ionization chamber 110 and the β-particles ionize samples 132 while in the gaseous phase, thereby forming positive ions, negative ions, and free electrons. Ionization chamber 110 is substantially a field-free region. Therefore, increasing a population density of the ions and electrons within ionization chamber 110 is facilitated as a function of the flux of β-particles. As the ions are being generated in ionization chamber 110 to increase the ion population therein, retaining grid 116 is maintained at a slightly greater potential than the potential of the ionization chamber 110 to induce a retention field and reduce the potential for ion leakage from ionization chamber 110. An electric field is then induced across ionization chamber 110 and, depending on the polarity of the induced electric field, the positive ions or the negative ions are pulsed from ionization chamber 110, through a high-voltage "kickout pulse", into a drift field region 112 through retaining grid 116. The ions of the opposite polarity are attracted to the walls of ionization chamber 110 and are discharged there. A second, reverse pulse follows the kickout pulse substantially instantaneously at the end of the kickout pulse. The pulses are controlled through ITMS control system 126 and are described further below.

Drift field region 112 extends from retaining grid 116 to the region defined by collector electrode 118 and collector shield grid 120. Drift field region 112 includes sequential, annular electrodes E1 through E5. Collector electrode 118 is positioned on the opposite side of drift field region 112 from ionization chamber 110 and is held at a ground potential. For those systems that use negative ions, annular electrodes E1 through E5 are energized to voltages that are sequentially less negative between ionization chamber 110 and collector electrode 118, thereby inducing a constant positive field. Motion is induced in the negative ions from the initial pulse in ionization chamber 110 and the ions are channeled through drift field region 112 to collector electrode 118 through collector shield grid 120. Collector shield grid 120 induces an electric field that is less negative that electrode E1 and is more negative than collector electrode 118 that is maintained at substantially ground potential. Signals representative of the ion population at collector electrode 118 are generated and transmitted to spectral analysis device 122 to determine the constituents in collected gas samples 132.

The population of negative ions generated in ionization chamber 110 include low-mobility analytes and high-mobility analytes. The low-mobility analytes traverse drift field region 112 with a lower velocity than the high-mobility analytes due to the relatively greater mass of the low-mobility analytes as compared to the lighter high-mobility analytes. The low-mobility and high-mobility analytes pulsed into drift field region 112 from ionization chamber 110 typically form an ion disk (not shown in FIG. 1) with a predetermined axial width value and possibly a trailing ion tail. Such trailing ion tail defines an asymmetric peak trace on trace displays of spectral analysis device 122.

Figure 2:
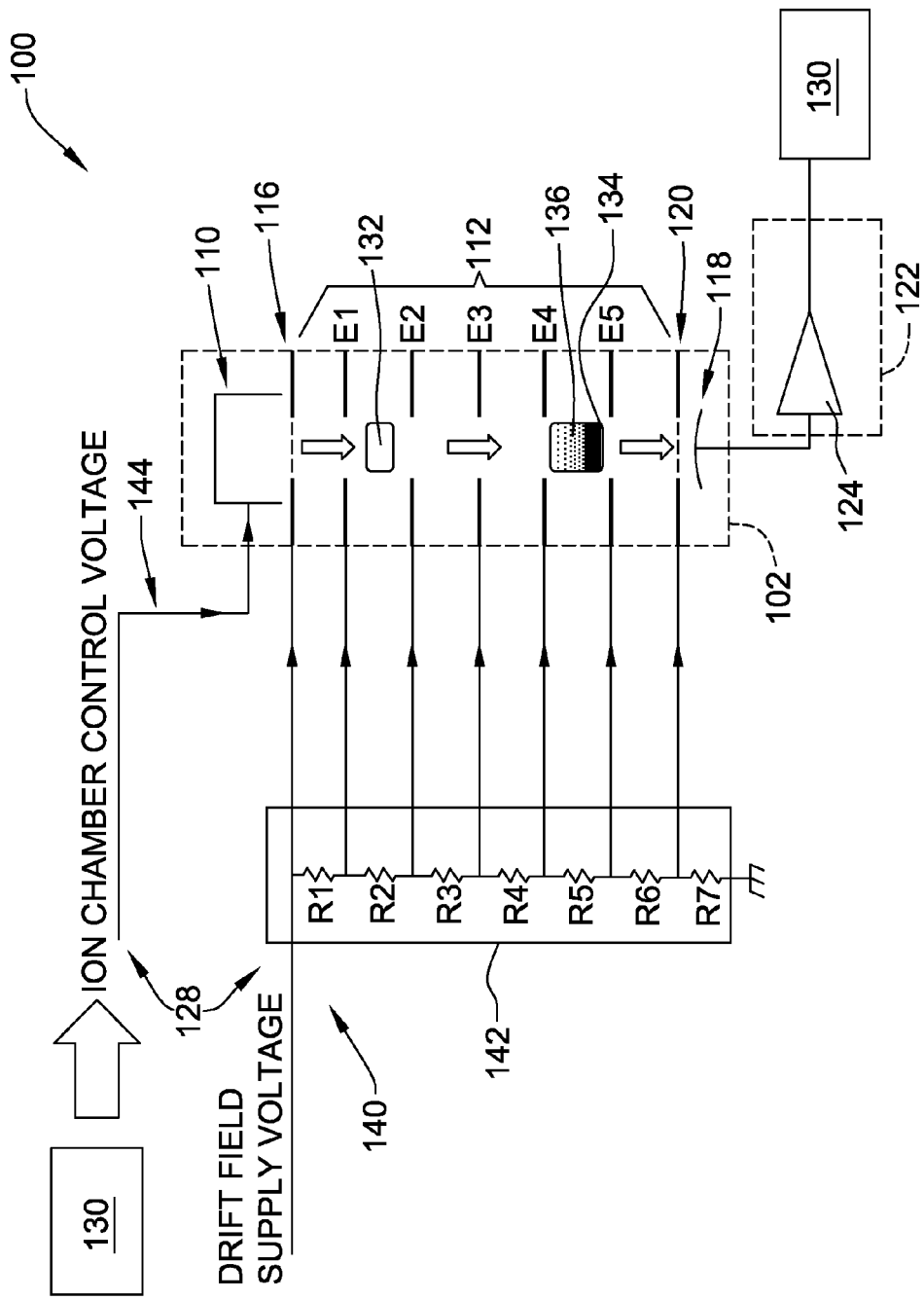

FIG. 2 is a schematic view of a portion of ITMS control system 126 that is used with ITMS detection system 100. ITMS control system 126 includes control circuit 128 and processing device 130. Control circuit 128 is coupled to ionization chamber 110, retaining grid 116, sequential annular electrodes E1, E2, E3, E4, and E5, and collector shield grid 120. Processing device 130 is operatively coupled to spectral analysis device 122 and control circuit 128.

Control circuit 128 includes a drift field supply voltage circuit 140 that includes a voltage divider circuit 142 that is coupled to a voltage supply (not shown in FIG. 2) that transmits a drift field supply voltage. Voltage divider circuit 142 is coupled to each of electrodes E1 thru E5, retaining grid 116, and collector shield grid 120. Voltage divider circuit 140 includes a plurality of resistors R1 through R7 that facilitate regulating the voltage of each of electrodes E1 thru E5 and both grids 116 and 120, where retaining grid 116 receives drift field supply voltage and collector shield grid 120 is energized after a predetermined voltage drop. Alternatively, voltage divider circuit 142 includes any configuration that enables operation of ITMS control system 126 and ITMS detection system 100 as described herein.

For those systems that use negative ions, voltage divider circuit 142 facilitates energizing annular electrodes E1 through E5 at voltages that are sequentially less negative between ionization chamber 110 and collector electrode 118, thereby inducing a substantially constant positive field. Motion is induced in the negative ions from the initial pulse in ionization chamber 110 and the ions are channeled through drift field region 112 to collector electrode 118 through collector shield grid 120. Collector shield grid 120 induces an electric field that is less negative that electrode E1 and is more negative than collector electrode 118 that is maintained at substantially ground potential.

Control circuit 128 also includes an ion chamber control voltage circuit 144 (only a portion shown in FIG. 2) that is coupled to a voltage supply (not shown in FIG. 2) that transmits an ion chamber control voltage in the form of kickout pulses and reverse pulses as regulated by processing device 130. Specifically, processing device 130 controls ion chamber control voltage to ionization chamber 110. An electric field is then induced across ionization chamber 110 and, depending on the polarity of the induced electric field, the positive ions or the negative ions are pulsed from ionization chamber 110, through the high-voltage kickout pulse, into drift field region 112 through retaining grid 116. A second, reverse pulse is transmitted through ion chamber control voltage circuit 144 and is regulated by processing device 130 such that the reverse pulse follows the kickout pulse substantially instantaneously at the end of the kickout pulse.

For purposes of comparison, FIG. 2 shows a first ion disk 132 transiting drift field region 112 that is a result of a kickout pulse and a reverse pulse as compared to a second ion disk 134 with a tailing portion 136 that is a result of a kickout pulse only.

Figure 3:
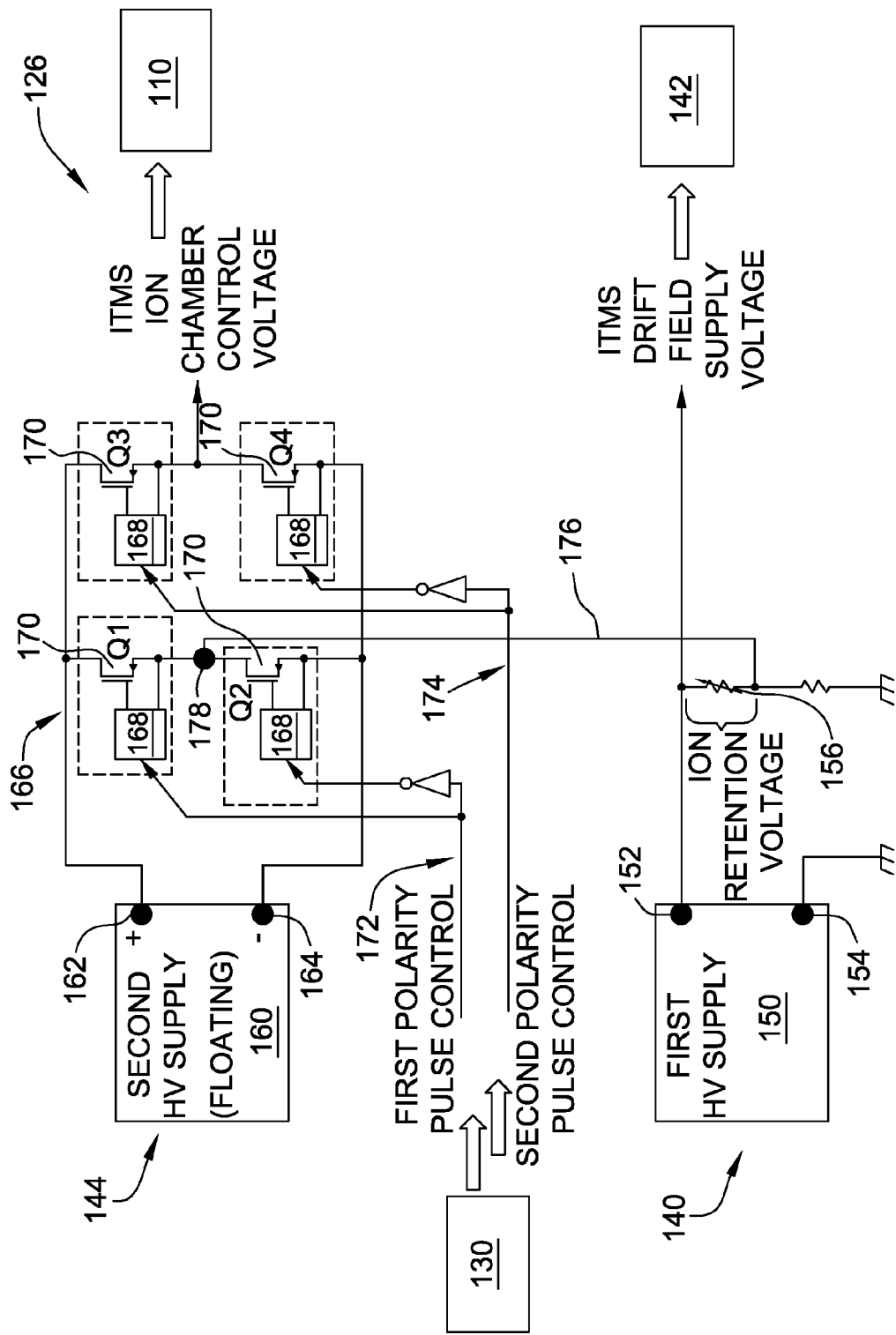

FIG. 3 is a schematic view of another portion of ITMS control system 126 that may be used with ITMS detection system 100 (shown in FIGS. 1 and 2). Control circuit 128 includes drift field supply voltage circuit 140 that includes voltage divider circuit 142. Drift field supply voltage circuit 140 also includes a first high voltage (HV) power supply 150. In the exemplary embodiment, HV power supply 150 includes a HV terminal 152 that is energized to any voltage value that enables operation of circuit 140 as described herein. HV power supply 150 also includes a ground terminal 154. Circuit 140 further includes an ion retention voltage rheostat 156 that is configured to vary the value of the drift field supply voltage to first retention grid 116 (shown in FIG. 2) to facilitate ion retention within ion chamber 110 (shown in FIG. 2). Ion retention voltage rheostat 156 is adjustable through either of manual adjustments and operation through processing device 130. In some alternative embodiments, a potentiometer or an electronic voltage regulator are used in place of rheostat 156.

Control circuit 128 also includes ion chamber control voltage circuit 144 that includes a second high voltage (HV) power supply 160. In the exemplary embodiment, HV power supply 160 is a floating power supply that includes a positive terminal 162 and a negative terminal 164 that are energized to any voltage values that enable operation of circuit 144 as described herein.

Ion chamber control voltage circuit 144 also includes a fast-switching high voltage transistor bridge circuit 166, i.e., four drive devices Q1, Q2, Q3, and Q4. Each of drive devices Q1 through Q4 are substantially similar and, in the exemplary embodiment, include a HV photovoltaic-driver 168 coupled to a HV transistor 170. In the exemplary embodiment, bridge circuit 166 provides voltage pulses with amplitudes in the range between 500 volts (V) and 1,500V, depending on the field existing in ITMS drift region 112, in order to eject the ions quickly and efficiently. Alternatively, HV transistors 170 are driven with equipment including, without limitation, pulse transformers, opto-couplers with associated power sources, and ceramic resonator isolators. Also, in some embodiments, alternative circuits are used to produce the kick-out pulses, including without limitation, a circuit with three HV switch devices connected to three distinct HV levels, and circuits at ground potential and coupled to ion chamber 110 through capacitors and/or transformers.

Processing device 130 is coupled to all four drive devices Q1 through Q4. Specifically, processing device 130 is coupled to Q1 and to Q2 through a first polarity pulse control circuit 172 and coupled to Q3 and to Q4 through a second polarity pulse control circuit 174. As such, ion chamber control voltage circuit 144 transmits voltage pulses to ion chamber 110 of predetermined durations, polarities, voltage amplitudes, and sequencing. Circuit 144 is coupled to circuit 140 though a conduit 176 that elevates a circuit common terminal 178 of bridge circuit 166 from ground potential by the amount of the ITMS drift potential.

Each HV opto-drive 168 provides for an isolated method for driving associated HV transistor 170. In general, by commanding one or the other pairs of transistors in the bridge legs to switch states, either polarity output pulse may be obtained. There are three logic states, i.e., no pulse, positive pulse, and negative pulse. The pulse widths are determined by processing device 130.

Figure 4:
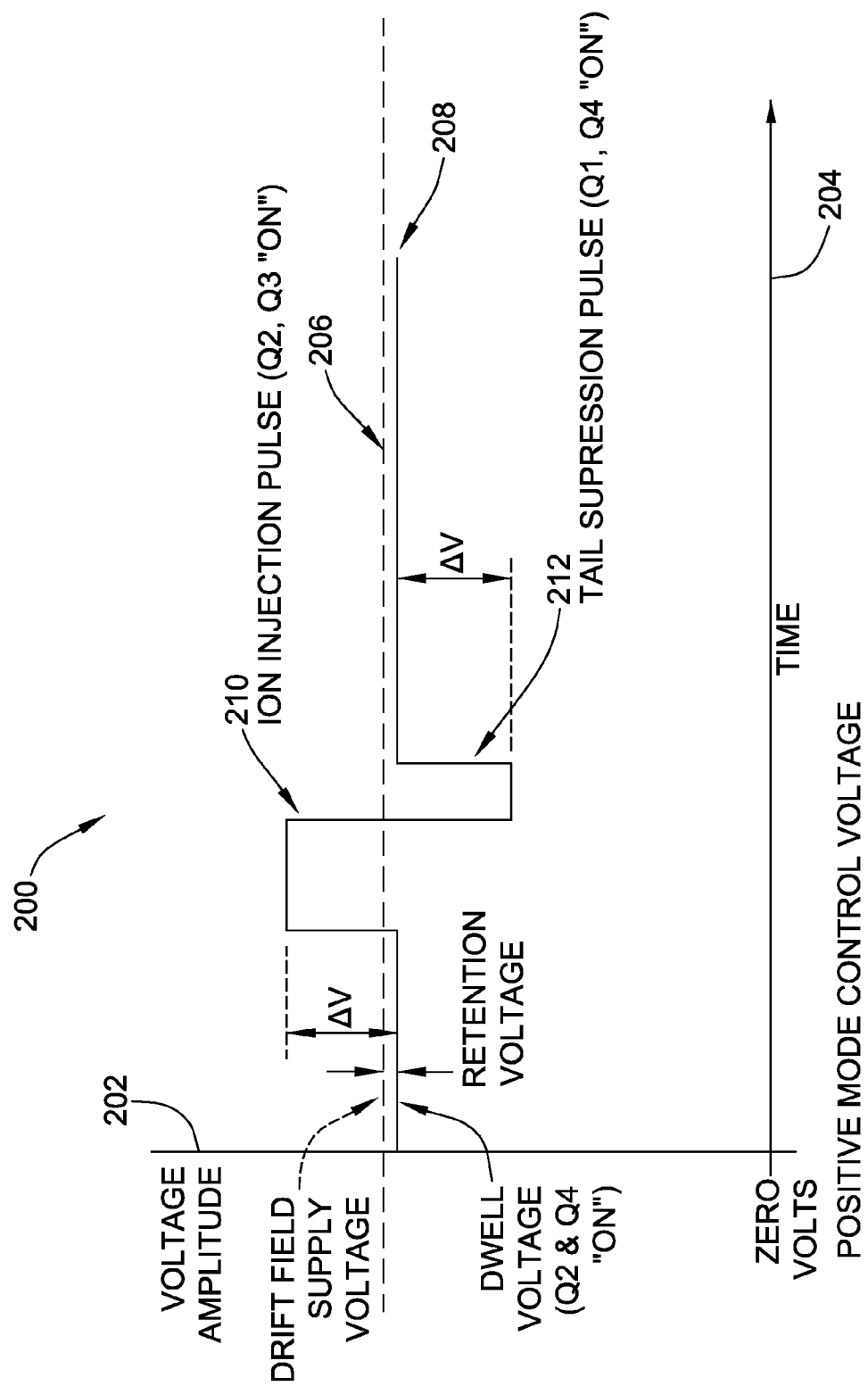

FIG. 4 is a graphical view of a positive mode control voltage waveform 200 that may be used with ITMS control system 126 (shown in FIGS. 2 and 3). Positive mode control voltage waveform 200 includes a y-axis 202 that represents a voltage amplitude of the pulses and an x-axis 204 that represents time. Both y-axis 202 and x-axis 204 are unitless. Drift field supply voltage is represented by dashed line 206 and is substantially constant. A dwell voltage 208 is induced when drive devices Q2 and Q4 (both shown in FIG. 3) are in an "ON" state. Positive mode control voltage waveform 200 also includes a positive ion injection pulse 210 when drive devices Q2 and Q3 (shown in FIG. 3) are in an "ON" state. Waveform 200 further includes a tail suppression pulse when drive devices Q1 (shown in FIG. 3) and Q4 are in an "ON" state. A difference between drift field supply voltage 206 and dwell voltage 208 is the retention voltage associated with retaining ions in ion chamber 110.

Ion injection pulse 210 has a positive polarity that has a predetermined voltage amplitude, depending on the field existing in ITMS drift region 112 (shown in FIGS. 1 and 2) in order to eject the ions quickly enough. Pulse 210 has a temporal duration within a predetermined range programmable within processing device 130 (shown in FIGS. 1-3). In addition, second, reverse pulse 212 is transmitted substantially instantly after ion injection pulse 210 to suppress ion tails. Pulse 212 has a voltage amplitude that is positive, however, it is reversed in polarity with respect to dwell voltage 208 such that both pulses 210 and 212 extend from dwell voltage 208 with similar values, i.e., $\Delta V$. Also, pulse 212 has a shorter width than pulse 210.

Figure 5:
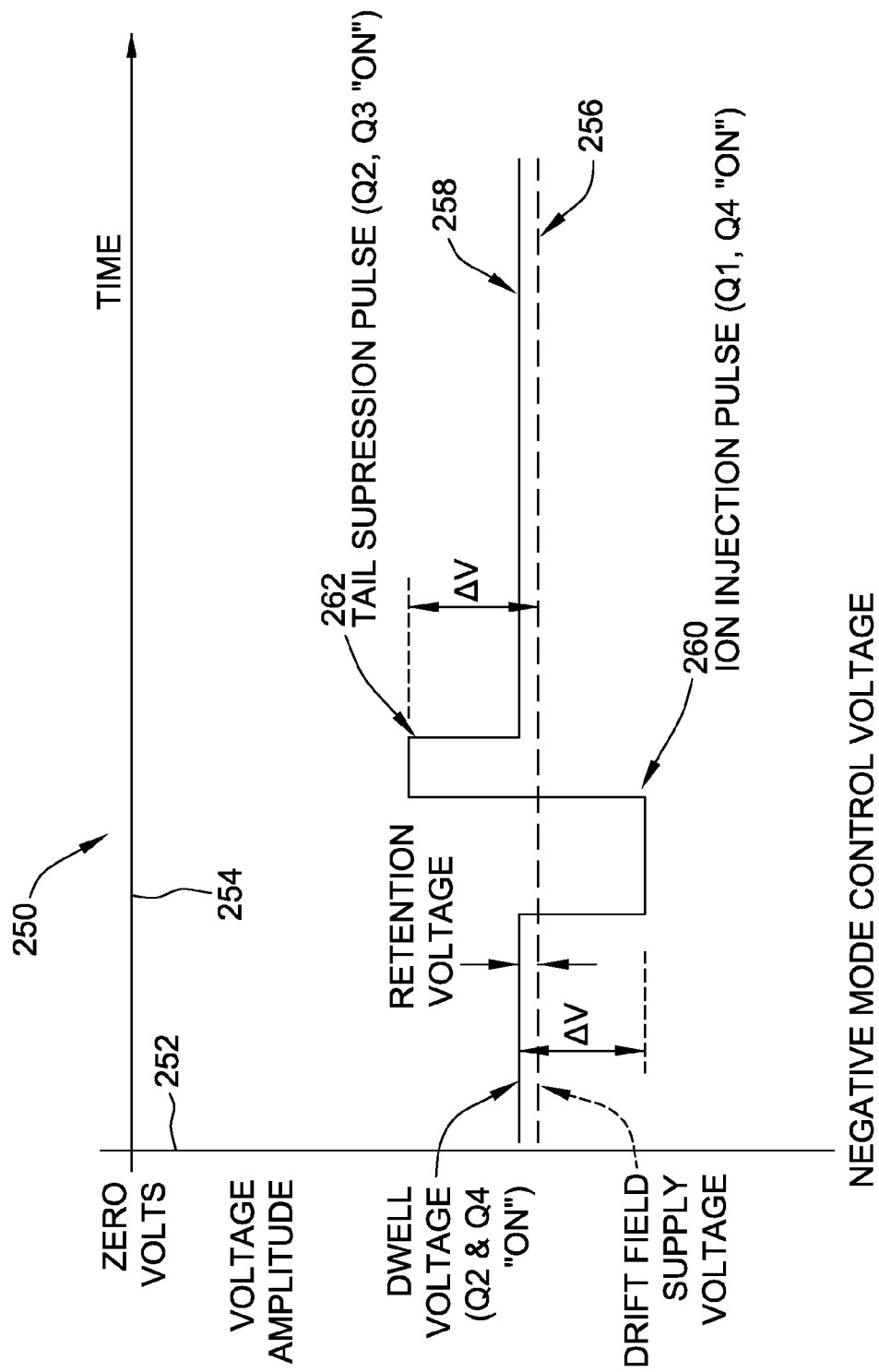

FIG. 5 is a graphical view of a negative mode control voltage waveform 250 that may also be used with ITMS control system 126 (shown in FIGS. 2 and 3). Negative mode control voltage waveform 250 includes a y-axis 252 that represents a voltage amplitude of the pulses and an x-axis 254 that represents time. Both y-axis 252 and x-axis 254 are unitless. Drift field supply voltage is represented by dashed line 256 and is substantially constant. A dwell voltage 258 is induced when drive devices Q2 and Q4 (both shown in FIG. 3) are in an "ON" state. Negative mode control voltage waveform 250 also includes a negative ion injection pulse 260 when drive devices Q2 and Q3 (shown in FIG. 3) are in an "ON" state. Waveform 250 further includes a tail suppression pulse when drive devices Q1 (shown in FIG. 3) and Q4 are in an "ON" state. A difference between drift field supply voltage 256 and dwell voltage 258 is the retention voltage associated with retaining ions in ion chamber 110.

Ion injection pulse 260 has a negative polarity that has a voltage amplitude in a predetermined range, depending on the field existing in ITMS drift region 112 (shown in FIGS. 1 and 2) in order to eject the ions quickly enough. Pulse 260 has a temporal duration within a predetermined range programmable within processing device 130 (shown in FIGS. 1-3). In addition, second, reverse pulse 262 is transmitted substantially instantly after ion injection pulse 260 to suppress ion tails. Pulse 262 has a voltage amplitude that is negative, however, it is reversed in polarity with respect to dwell voltage 258 such that both pulses 260 and 262 extend from dwell voltage 258 with similar values, i.e., $\Delta V$. Also, pulse 262 has a shorter width than pulse 260.

Figure 6:
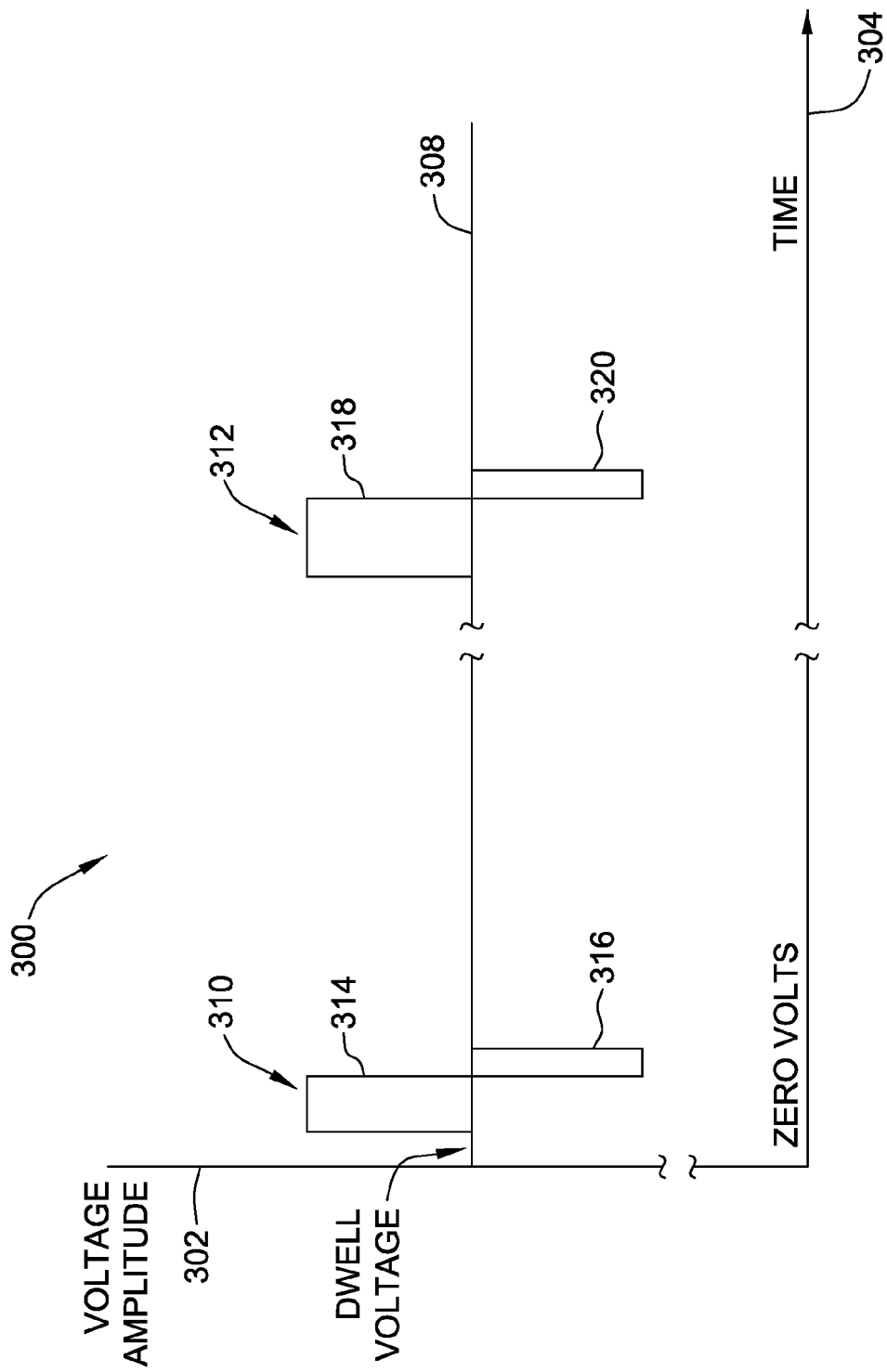

FIG. 6 is a graphical view of positive mode control voltage waveforms 300 for fast, i.e., high-mobility ions and slow, i.e., low-mobility ions that may be used with ITMS control system 126 (shown in FIGS. 2 and 3). Waveforms 300 are plotted against a y-axis 302 that represents a voltage amplitude of the pulses and an x-axis 304 that represents time. Both y-axis 302 and x-axis 304 are unitless. Waveforms 300 are referenced to a dwell voltage 308. In general, waveforms 300 include dual-resolution kickout pulse shapes for the positive polarity mode similar to those shown in FIG. 4. Specifically, a first set of pulses 310 is shown for those ions that have faster drift times, i.e., drift times in a range between 2.5 mS and 5.0 mS. A second set of pulses 312 is shown for those ions that have slower drift times, i.e., drift times greater than 5.0 mS. First set of pulses 310 includes an ion injection (kickout) pulse 314 followed by an ion tail suppression pulse 316. Similarly, second set of pulses 312 includes an ion injection (kickout) pulse 318 followed by an ion tail suppression pulse 320. Waveforms 300 show pulses with a positive polarity and waveforms similar to waveforms 250 (shown in FIG. 5) will be obtained using negative polarities.

In operation, ITMS detection system 100 (shown in FIGS. 1 and 2), using ITMS control system 126 (shown in FIGS. 1, 2, and 3) generates ion injection pulse 314 and ion tail suppression pulse 316 for high-mobility ions. After a predetermined temporal period, ITMS control system 126 generates ion injection pulse 318 and ion tail suppression pulse 320 for low-mobility ions. Processor 130 (shown in FIGS. 1, 2, and 3)

regulates the pulse widths, polarities, pulse amplitudes, and temporal periodicities and intervals of waveforms 300.

Separate pulse sequences for low-mobility ions and high-mobility ions are generated such that the consecutive spectra recorded alternate between being optimized for high-mobility ions and low-mobility ions. The frequencies of such alternating pulse sequences are within a predetermined range, where the resulting data either is combined and evaluated or evaluated separately. Therefore, a potential effect of using the reverse ion suppression pulses to truncate the ion injections into drift field region 112 (shown in FIGS. 1 and 2) is reduced. Specifically, a reduction in the width of the kickout pulses may favor injection of the high-mobility ions, thereby decreasing a sensitivity of ITMS detection system 100 with respect to low-mobility ions.

Figure 7:
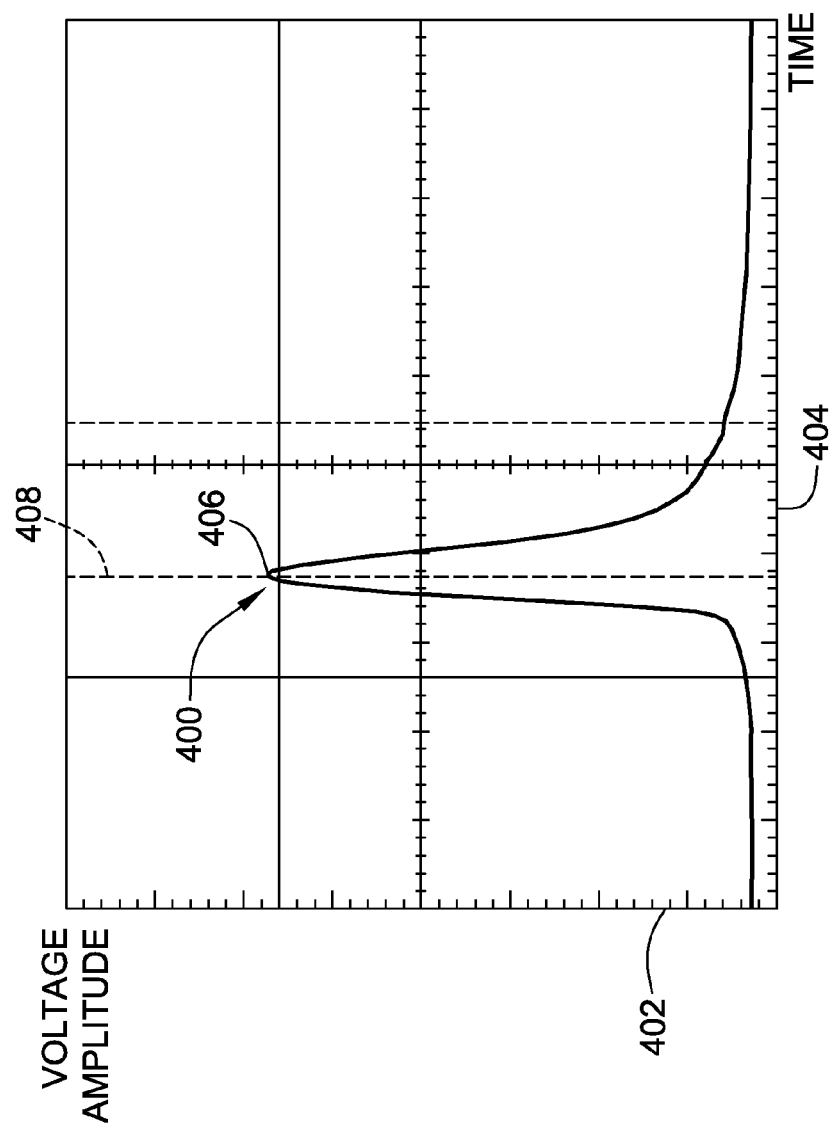

FIG. 7 is a graphical view of a primary reactant peak spectrum 400, i.e., a portion of a broader spectrum generated by ITMS detection system 100 (shown in FIGS. 1 and 2) without a reverse pulse. Primary reactant peak spectrum 400 is plotted with respect to a y-axis 402 that represents voltage amplitude and with respect to an x-axis 404 that represents time. Primary reactant peak spectrum 400 includes a peak 406. A vertical marker line 408 is shown running through, and bisecting peak 406.

Figure 8:
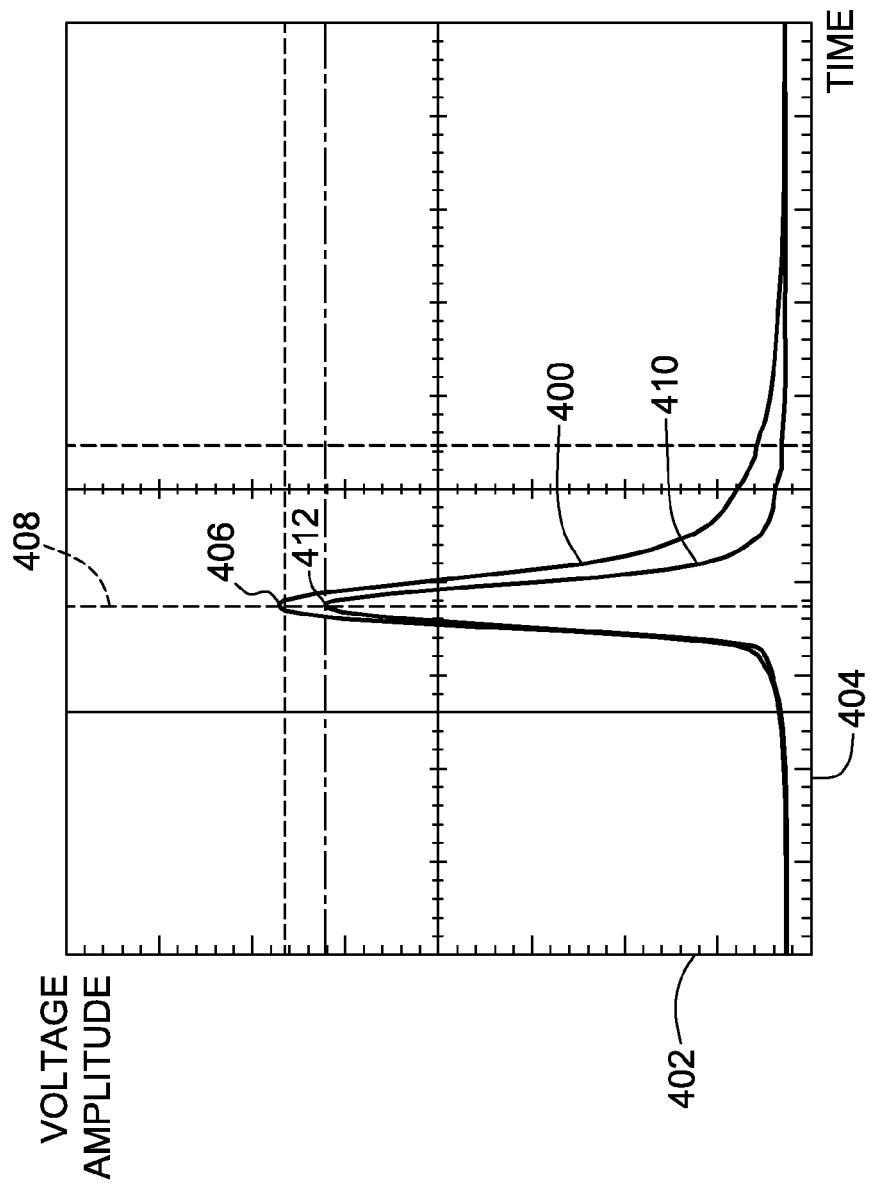

FIG. 8 is a graphical view of primary reactant peak spectrum 400 with a primary reactant peak spectrum 410, i.e., a portion of a broader spectrum generated by ITMS detection system 100 (shown in FIGS. 1 and 2) resulting from adding the reverse pulse and superimposed on primary reactant peak spectrum 400. Primary reactant peak spectrum 410 is plotted with respect to y-axis 402 that represents voltage amplitude and with respect to x-axis 404 that represents time. Primary reactant peak spectrum 410 includes a peak 412.

The reverse pulse lowers the amplitude somewhat as a function of a decreased total ion count within ion disk 132 (shown in FIG. 2) ejected out of ionization chamber 110 (shown in FIGS. 1 and 2) as a result of the ion suppression pulse. This results in a slight decrease in spectrum peak amplitude (about 4%). Also, the ion suppression pulse decreases the width of the trace by about 16%, which improves resolution by decreasing tailing portion 136 of ion disk 134 (both shown in FIG. 2). Decreasing the width of peak spectrum 400 to that of peak spectrum 410 through the use of an ion suppression pulse decreases a peak asymmetry factor that is a function of a ratio of a distance between vertical marker line 408 and the tailing portion of peak spectra 400 and 410 on the right hand side and a distance between vertical marker 408 and the left hand side of peak spectra 400 and 410, i.e., the larger the tailing portion width the larger the peak asymmetry factor.

Figure 9:
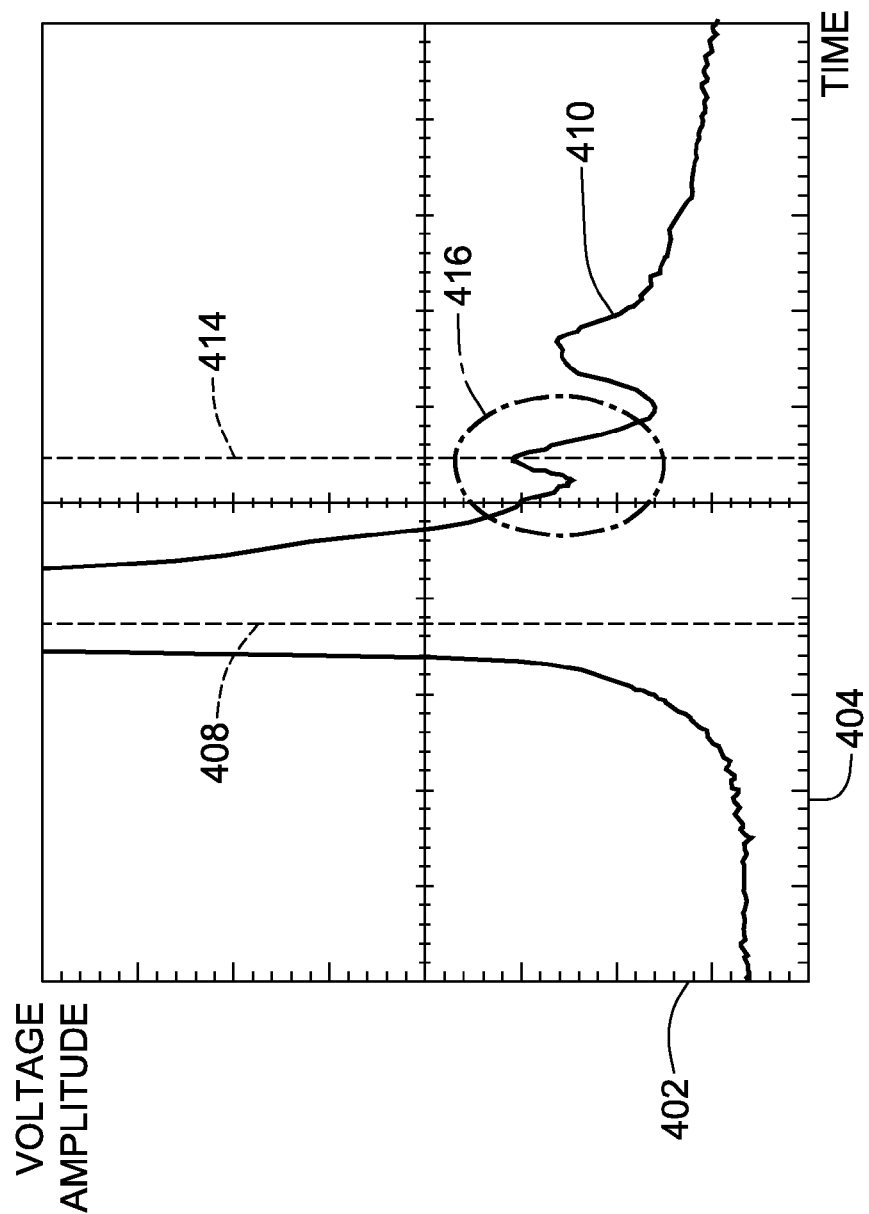
Figure 10:
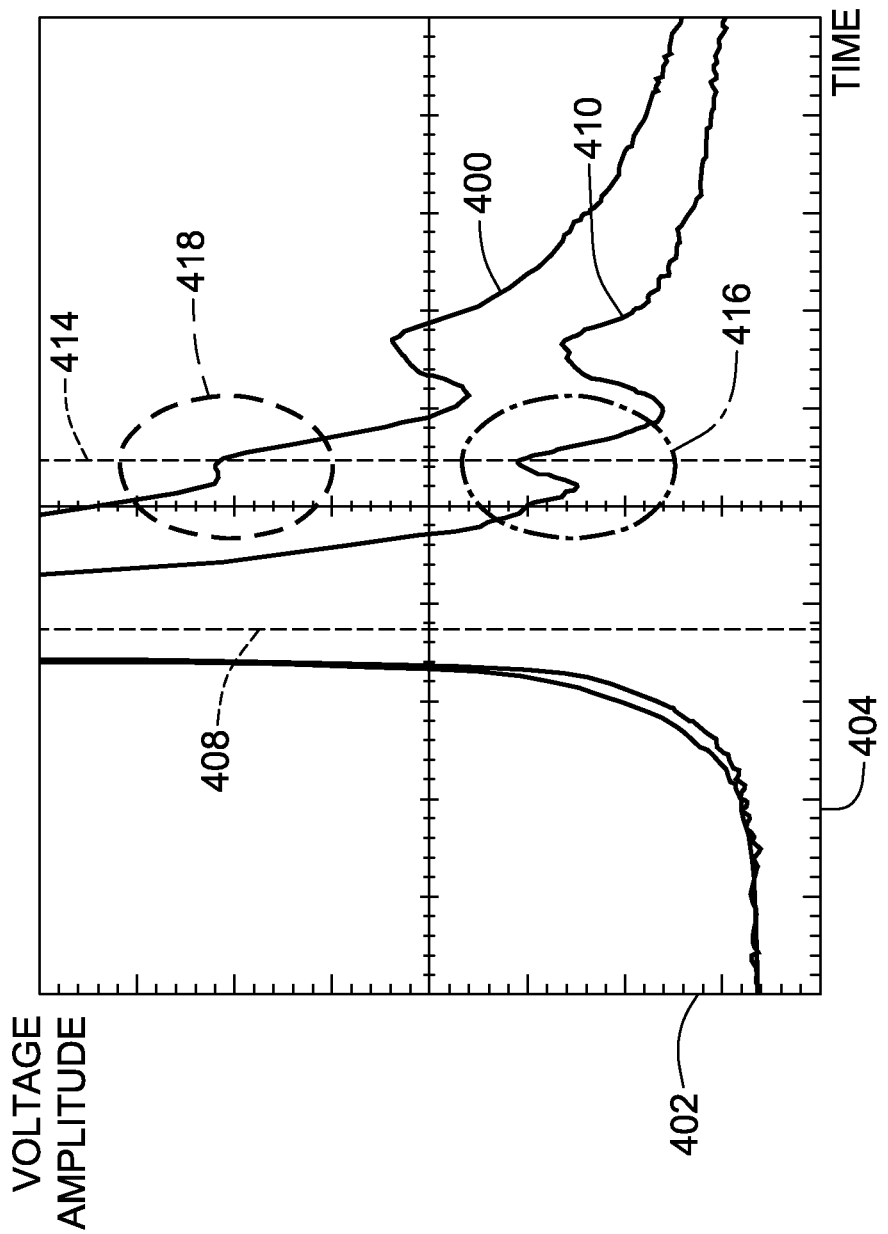

FIG. 9 is a magnified graphical view of a portion of primary reactant spectrum peak spectrum 410. FIG. 10 is a magnified graphical view of a portion of reactant spectrum peak spectrum 410 with a portion of primary reactant peak spectrum 400 superimposed thereon. A vertical marker line 414 is shown running through a small additional spectrum peak 416 riding on reactant peak spectrum 410 that is due to a small amount of chemical analyte present in both trace samples. A less discernible peak 418 of primary reactant peak spectrum 400 is also shown with vertical marker line 414 running therethrough. Peak 416 is clearly discernible due to the increased resolution of peak spectrum 410.

Figure 11:
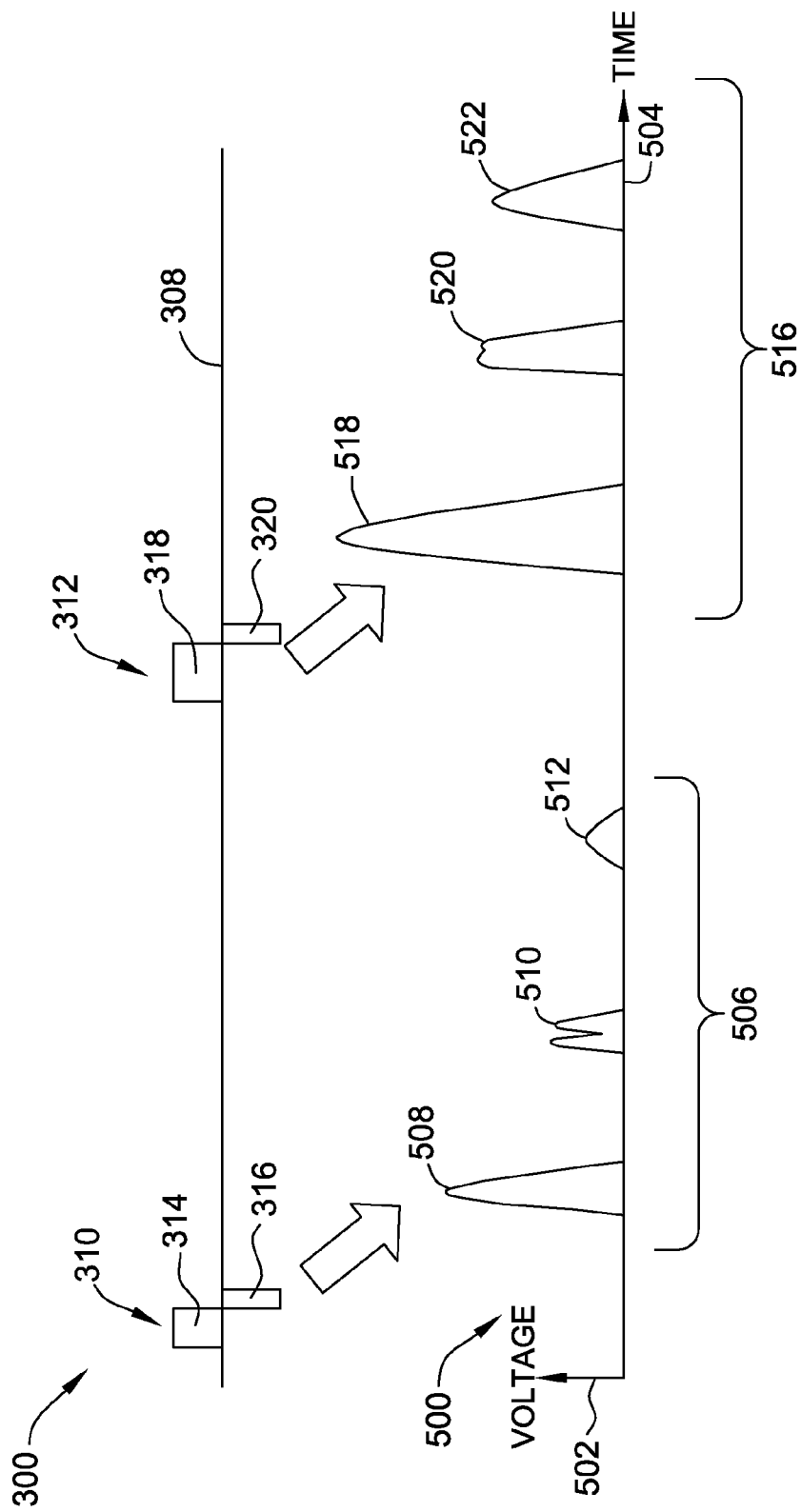

FIG. 11 is a graphical view of positive mode control voltage waveforms 300 for fast, i.e., high-mobility ions and slow, i.e., low-mobility ions from FIG. 6 and resultant spectra 500 optimized for high-mobility and low-mobility ions. As described above, waveforms 300 include dual-resolution kickout pulse shapes for the positive polarity mode similar to those shown in FIG. 4. Specifically, a first set of pulses 310 is shown for those ions that have faster drift times, i.e., drift times in a range between 2.5 mS and 5.0 mS. A second set of pulses 312 is shown for those ions that have slower drift times, i.e., drift times greater than 5.0 mS. First set of pulses 310 includes an ion injection (kickout) pulse 314 followed by an ion tail suppression pulse 316. Similarly, second set of pulses 312 includes an ion injection (kickout) pulse 318 followed by an ion tail suppression pulse 320. As such, spectra generation is alternated between a spectrum enhanced for fast ions followed by a spectrum enhanced for slow ions.

Pulse 318 is wider than pulse 314 with a predetermined percentile increase that is configurable within ITMS control system 126. The widths of pulses 314 and 318 are configurable to be either static or variable, and such selection is further configured to be one of manual and automatic as a function of, without limitation, the analytes of interest. Also, in a manner similar to that associated with configuring the pulse lengths, the temporal separation of first set of pulses 310 and second set of pulses 312 is configurable with respect to static or variable temporal separations. As such, ITMS control system 126 sends the correct pulse widths at the start of every spectrum.

Spectra 500 are plotted with respect to a y-axis 502 that represents voltage amplitude and with respect to an x-axis 504 that represents time. Spectra 500 includes a first spectrum 506 enhanced for those ions that have faster drift times, i.e., high-mobility ions. First spectrum 506 includes a first primary reactant peak 508, a resolved pair of high-mobility ion peaks 510, and a first low-mobility ion peak 512. Spectra 500 also includes a second spectrum 516 enhanced for those ions that have slower drift times, i.e., low-mobility ions. Second spectrum 516 includes a second primary reactant peak 518, an unresolved pair of high-mobility ion peaks 520, and a second low-mobility ion peak 522.

As compared to second spectrum 516, first spectrum 506 includes first primary reactant peak 508 that is lower and narrower than second primary reactant peak 518. This effect is primarily due to the extended width of kickout pulse 318, as compared to kickout pulse 314, injecting a larger number of ions. Also, as compared to second spectrum 516, first spectrum 506 includes resolved pair of high-mobility ion peaks 510 in contrast to unresolved pair of high-mobility ion peaks 520. This effect is primarily due to the lighter, higher-mobility ions of differing materials with a relatively greater difference in their masses being temporally separated during transport through drift field region 112 (shown in FIG. 1) as compared to the slower, lower-mobility ions that do not temporally separate due to a smaller relative difference between the masses of the heavier differing materials. Further, as compared to second spectrum 516, first spectrum 506 includes a smaller first low-mobility ion peak 512 as compared to second low-mobility ion peak 522. This effect is primarily due to the extended width of kickout pulse 318, as compared to kickout pulse 314, injecting a larger number of lower-mobility ions.

Waveforms 300 show pulses with a positive polarity and waveforms similar to waveforms 250 (shown in FIG. 5) will be obtained using negative polarities. As such, the resultant spectra from negative polarity pulses would be pointing downward in contrast to spectra 500 that are all pointing upward. In addition, the peak sizes and locations in the opposite polarity will likely be different because the negative polarity pulses ejected ions different than positive polarity pulses. Moreover, the shifting of polarities between positive and negative alternates with a frequency within a range between 10 times per second and 100 times per second, such frequencies depending on the size of the detector and the voltage ratings of the system. For example, smaller detectors and higher voltages facilitate higher frequencies of alternating between positive and negative polarities.

Data storage device 132 (shown in FIG. 1) receives the spectral data associated with each spectrum of spectra 500 and stores it within data records therein. The spectra data records include data elements such as, and without limitation, pulse widths (for slow and fast ions) and polarities (positive and negative).

The ITMS detection systems described herein provide a cost-effective system and method for improving detection of materials of interest from an object or person. The systems and methods described herein induce a first electric field across an ionization chamber for a first temporal period, i.e., a first pulse. The first pulse has a first polarity, thereby ejecting at least a portion of the ions from the ionization chamber. Also, the systems and methods described herein induce a second electric field across the ionization chamber substantially immediately following the first temporal period. The second electric field has a second polarity opposite the first polarity, i.e., a second pulse, thereby substantially decreasing the ejection of the at least a portion of the ions from the ionization chamber. Further, the systems and methods described herein reduce a peak tailing portion of a spectral trace associated with the ions ejected from the ionization chamber as a result of the second field pulse. Moreover, the first and second pulses are regulated such that more precise ion injection is achieved and increased resolution of high-mobility analytes is facilitated.

A technical effect of the systems and methods described herein includes at least one of: (a) inducing a first electric field across an ionization chamber for a first temporal period, wherein the first electric field has a first polarity, thereby ejecting at least a portion of the ions from the ionization chamber, and inducing a second electric field across the ionization chamber substantially immediately following the first temporal period, wherein the second electric field has a second polarity opposite the first polarity, thereby substantially decreasing the ejection of the at least a portion of the ions from the ionization chamber; (b) reducing a peak tailing portion of a spectral trace associated with the ions ejected from the ionization chamber; and (c) regulating the first and second pulses such that more precise ion injection is achieved and increased resolution of high-mobility analytes is facilitated.

Exemplary embodiments of ion trap mobility spectrometer (ITMS) detection systems and methods of using the same are described above in detail. The methods and systems are not limited to the specific embodiments described herein, but rather, components of systems and/or steps of the methods may be utilized independently and separately from other components and/or steps described herein. For example, the methods may also be used in combination with other detection systems and methods, and are not limited to practice with only the detection systems and methods as described herein. Rather, the exemplary embodiment may be implemented and utilized in connection with many other detection applications.

Although specific features of various embodiments of the invention may be shown in some drawings and not in others, this is for convenience only. In accordance with the principles of the invention, any feature of a drawing may be referenced and/or claimed in combination with any feature of any other drawing.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. An apparatus for detecting constituents in a sample, said apparatus comprising:
   a casing;
   an ionization chamber at least partially defined by said casing, said ionization chamber configured to generate and store ions;
   an ion collector positioned downstream of said ionization chamber;
   a spectral analysis device coupled to said ion collector, said spectral analysis device configured to generate a detection spectrum representative of ions collected at said ion collector, wherein the detection spectrum includes an analyte peak portion and a peak tailing portion; and
   a control system coupled to said ionization chamber, said control system configured to:
   generate a first pulse within said ionization chamber, the first pulse having a first polarity to initiate a discharge of at least a portion of the stored ions from said ionization chamber; and
   generate a second pulse within said ionization chamber, the second pulse having a second polarity opposite the first polarity of the first pulse that is generated substantially immediately after the first pulse, wherein the second pulse is configured to reduce a peak tailing portion.

2. The apparatus in accordance with claim 1, wherein the first pulse has a first duration and the second pulse has a second duration that is less than the first duration.

3. The apparatus in accordance with claim 1, wherein the first pulse has a first voltage amplitude and the second pulse has a second voltage amplitude that is similar in absolute value to the first voltage amplitude.

4. The apparatus in accordance with claim 1, wherein the first pulse comprises a plurality of first pulses and the second pulse comprises a plurality of second pulses, wherein said plurality of first pulses and said plurality of second pulses at least partially generate at least one detection spectrum on said spectral analysis device comprising at least one of:
   a first detection spectrum representative of detected high-mobility ions; and
   a second detection spectrum representative of detected low-mobility ions.

5. The apparatus in accordance with claim 4, wherein the first detection spectrum representative of detected high-mobility ions includes a plurality of high-mobility ion spectra representative of alternating ion polarities.

6. The apparatus in accordance with claim 4, wherein the second detection spectrum representative of detected low-mobility ions includes a plurality of low-mobility ion spectra representative of alternating ion polarities.

7. The apparatus in accordance with claim 1, wherein said control system is further configured to generate a pulse cycle having each of a positive polarity and a negative polarity comprising:
   a pulse configured to eject high-mobility ions from the ionization chamber; and a pulse configured to eject low-mobility ions from the ionization chamber.

8. The apparatus in accordance with claim 1, wherein said control system is further configured to induce the second pulse to reduce a tailing portion of an ion disk generated through the first pulse.

9. The apparatus in accordance with claim 1, wherein the peak tailing portion defines a peak asymmetry factor, said control system is further configured to generate the second pulse to decrease the peak asymmetry factor.

10. The apparatus in accordance with claim 1 further comprising at least one processor configured to regulate at least one of:
   a polarity of each of the first pulse and the second pulse;
   a voltage amplitude of each of the first pulse and the second pulse;
   a temporal width of each of the first pulse and the second pulse; and
   a temporal interval between successive groupings of the first pulse with the second pulse.

11. A method of detecting constituents in a sample, said method comprising:
   channeling a sample gas stream to be tested for constituents into an ionization chamber;
   generating a plurality of ions in the ionization chamber;
   storing the plurality of ions in the ionization chamber;
   inducing a first electric field across the ionization chamber for a first temporal period, wherein the first electric field has a first polarity, thereby ejecting at least a portion of the ions from the ionization chamber; and
   inducing a second electric field across the ionization chamber substantially immediately following the first temporal period, wherein the second electric field has a second polarity opposite the first polarity, thereby substantially decreasing the ejection of the at least a portion of the ions from the ionization chamber.

12. The method in accordance with claim 11, wherein:
   inducing the first electric field comprises inducing a first pulse within the ionization chamber having a first duration; and
   inducing the second electric field comprises inducing a second pulse within the ionization chamber having a second duration that is less than the first duration.

13. The method in accordance with claim 11, wherein:
   inducing the first electric field comprises inducing a first pulse within the ionization chamber having a first voltage amplitude; and
   inducing the second electric field comprises inducing a second pulse within the ionization chamber having a second voltage amplitude that is similar in absolute value to the first voltage amplitude.

14. The method in accordance with claim 11, wherein inducing the first electric field comprises inducing a plurality of first pulses and inducing the second electric field comprises inducing a plurality of second pulses, wherein inducing the plurality of first pulses and inducing the plurality of second pulses comprises generating a plurality of detection spectra on a spectral analysis device coupled to an ion collector comprising:
   generating a first detection spectrum representative of high-mobility ions; and
   generating a second detection spectrum representative of low-mobility ions.

15. The method in accordance with claim 14, wherein:
   generating at least one first detection spectrum representative of high-mobility ions comprises generating a plurality of high-mobility ion spectra representative of alternating ion polarities; and
   generating at least one second detection spectrum representative of low-mobility ions comprises generating a plurality of low-mobility ion spectra representative of alternating ion polarities.

16. The method in accordance with claim 11, wherein inducing the first electric field and inducing the second electric field comprises generating a pulse cycle defined by at least one pulse having one of a positive polarity and a negative polarity, the at least one pulse configured to eject high-mobility ions from the ionization chamber.

17. The method in accordance with claim 11, wherein inducing the first electric field and inducing the second electric field comprises generating a pulse cycle defined by at least one pulse having one of a positive polarity and a negative polarity, the at least one pulse configured to eject low-mobility ions from the ionization chamber.

18. The method in accordance with claim 17, wherein generating a pulse cycle comprises regulating at least one of:
   a polarity of each of the pulses;
   a voltage amplitude of each of pulses;
   a temporal width of each of the pulses; and
   a temporal interval between successive groupings of each of the pulses.

19. The method in accordance with claim 11, wherein inducing a second electric field comprises reducing a tailing portion of an ion disk generated through the first electric field.

20. The method in accordance with claim 19, wherein reducing a tailing portion of an ion disk generated through the first electric field comprises decreasing a peak asymmetry factor of at least one detection spectrum.

* * * * *